(12) United States Patent
Rauchschwalbe et al.

(10) Patent No.: US 6,441,182 B1
(45) Date of Patent: Aug. 27, 2002

(54) METHOD FOR THE PRODUCTION OF 2,6-DICHLORO-5-FLUORO-NICOTINIC ACID AND COARSE AND PARTICULARLY PURE 2,6-DICHLORO-5-FLUORO-NICOTINIC ACID

(75) Inventors: Günter Rauchschwalbe, Leverkusen; Bernd Griehsel, Bottrop; Andreas Sattler, Wermelskirchen; Karsten von dem Bruch, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/009,437

(22) PCT Filed: Jun. 10, 1999

(86) PCT No.: PCT/EP00/04871

§ 371 (c)(1),
(2), (4) Date: Dec. 6, 2001

(87) PCT Pub. No.: WO00/76978

PCT Pub. Date: Dec. 21, 2000

(30) Foreign Application Priority Data

Jun. 10, 1999 (DE) .......................... 199 26 400

(51) Int. Cl.⁷ ............................. C07D 213/80
(52) U.S. Cl. ....................................... 546/318
(58) Field of Search ......................... 546/318

(56) References Cited

FOREIGN PATENT DOCUMENTS

| | | |
|---|---|---|
| EP | 0 132 845 | 2/1985 |
| EP | 0 160 578 | 11/1985 |
| EP | 0 191 451 | 8/1986 |
| EP | 0 333 020 | 9/1989 |
| GB | 2158825 | 11/1985 |
| GB | 2191776 | 12/1987 |
| WO | 96/04247 | 2/1996 |
| WO | 98/39298 | 9/1998 |

OTHER PUBLICATIONS

*Miyamot T. et al: "Pyridonecarboxylic Acids as Antibacterial Agents. VIII. An Alternative Synthesis of Enoxacin Via Fluoronicotinic Acid Derivatives", Chemical and Pharmaceutical Bulletin, JP, Pharmaceutical Society of Japan, Tokyo, Bd. 35, Nr. 6, 1987, Seiten 2280–2285, XP002073588.

*T. Miyamoto et al.: "Fluorinated Pyrido'2,3–c!pyridazines. I. Reductive Cyclization of Ethyl 2–Diazo–2–(5–fluoro–2–halonicotinoyl)acetate with Trialkylphosphine" Chem. Pharm. Bull., Bd. 38, Nr. 12, 1990, Seiten 3211–7, XP002150275.

*Primary Examiner*—Patricia L. Morris
(74) *Attorney, Agent, or Firm*—Joseph C. Gil; Richard E. L. Henderson

(57) ABSTRACT

The invention relates to a method for the production of 2,6-dichloro-5-fluoronicotinic acid by hydrolyzing 2,6-dichloro-5-fluoro-3-cyanopyridine by (a) dissolving 2,6-dichloro-5-fluoro-3-cyanopyridine at 70 to 90° C. in sulfuric acid having a concentration of 90 to 99% by weight and hydrolyzing the 2,6-dichloro-5-fluoro-3-cyanopyridine at 70 to 100° C. to the corresponding carboxamide, (b) cooling the resultant reaction mixture to a temperature in the range from 10 to 65° C., (c) metering in water until the concentration of sulfuric acid is 55 to 75% by weight (calculated relative to the sulfuric acid employed in stage (a) and the water employed in stage (c)) while keeping the temperature between 30 and 65° C. during the addition of the first quarter of the water and keeping the temperature between 50 and 80° C. during the addition of the second quarter of the water, and (d) completing hydrolysis of the resultant mixture to 2,6-dichloro-5-fluoronicotinic acid at 70 to 110° C.

10 Claims, No Drawings

METHOD FOR THE PRODUCTION OF 2,6-DICHLORO-5-FLUORO-NICOTINIC ACID AND COARSE AND PARTICULARLY PURE 2,6-DICHLORO-5-FLUORO-NICOTINIC ACID 2,6-Dichloro-5-fluoronicotinic acid (=DCFNA) is an important intermediate for preparing quinolonecarboxylic acid derivatives of the naphthyridonecarboxylic acid type which are used for preparing broad-spectrum antibiotics (see EP-A 160 578, EP-A 132 845 and DE-A 35 14 076).

The use of DCFNA as intermediate for pharmaceuticals requires that DCFNA is available in high purity, with good yields and in an economic manner.

Some methods for the production of DCFNA have already been disclosed, in which 2,6-dichloro-5-fluoro-3-cyanopyridine (=DCFN nitrile) undergoes acid hydrolysis. However, these methods do not meet all the requirements mentioned above.

Thus, DCFNA can be obtained according to EP-A 160 578 by hydrolyzing DCFN nitrile in a mixture of acetic acid, water and sulfuric acid. After a reaction time of 16 hours, the required reaction product is isolated in a yield of only 51.5% (see-loc. cit., page 6), which is completely inadequate.

Our own investigations have shown that after a reaction time of 16 hours there was still 39.3% by weight unreacted DCFN nitrile, but 4.7% by weight of the DCFNA had already decomposed, whereas after a reaction time of 32 hours there was still 23.4% by weight unreacted DCFN nitrile, 3.2% by weight of the corresponding carboxamide were present, and the proportion of decomposition products had risen to 8.2% by weight (see comparative example 4). It is accordingly not possible to achieve a significant improvement in the yields by shortening or lengthening the hydrolysis time. Chem. Pharm. Bull. 38, 3211–3217 (1990) describes the hydrolysis of DCFN nitrile initially at 65 to 75° C. with 96% by weight sulfuric acid within one hour to the corresponding carboxamide, dilution of the mixture which is then present and contains 99% by weight sulfuric acid by addition of water within 30 minutes at a controlled temperature below 100° C. in such a way that the resulting mixture contains about 65% by weight sulfuric acid, and completion of the hydrolysis to DCFNA at 100 to 110° C. After renewed dilution, this time to 48% by weight sulfuric acid, crude DCFNA is removed in a yield of 90.5%. However, based on the DCFNA content in the crude product, the yield is only 84.1% (see comparative example 1). The crude product contains 6.6% by weight decomposition products. Even these features make this method uninteresting for industrial application. An additional factor is that the dilution of sulfuric acid with water is very exothermic, so that temperature control is possible if at all only with small reaction batches and slow addition of water, but not with batches on the industrial scale with rapid addition of water. This is therefore only a laboratory method which cannot be transferred to the industrial scale.

Our own experiments have shown that lengthening the metering time for the water for dilution to an extent necessary to make temperature control possible in industrial plants leads to a large increase in the decomposition of DCFNA which has already been formed (see comparative example 2). This leads to a further unacceptable reduction in yield and deterioration in the product.

A modification of this method in which water is metered in isothermally at 0 to 5° C. (see WO 98/39298, example 1 c), is likewise of no interest for the industrial scale because a cooling medium at least 20° C. cooler would be necessary to remove the heat, which could be provided and handled only with unacceptably high apparatus costs.

In another method (see EP-A 333 020), DCFN nitrile is hydrolyzed in concentrated sulfuric acid within 45 minutes at 75° C. to the carboxamide, then, after cooling to 0° C., conc. hydrochloric acid is added to the mixture, which is finally heated to boiling for one hour and, after cooling, DCFNA is isolated. The yield is only 19.5%, which is extremely low.

A variant of this method (see WO 98/39298) consists of the carboxamide intermediate being isolated by discharging the reaction mixture onto ice and extraction with a propanol/chloroform mixture, and then being hydrolyzed with conc. hydrochloric acid to DCFNA. Although this increases the yield to 58%, this is still far from satisfactory and the industrial costs necessary for the intermediate isolation and extraction are unreasonably high.

Another method variation described in WO 98/39298 uses the method of diazotizing hydrolysis with nitrous acid to hydrolyze the carboxamide to DCFNA. A large excess of nitrous acid is necessary in this case, and the isolated crude product requires an extremely industrially complicated workup (extraction with an ether, washing of the ether extract with water, extraction of the washed ether phase with sodium carbonate solution and acidification of the enriched sodium carbonate solution to precipitate DCFNA). The use of excess nitrous acid leads to the generation of large amounts of nitrous gases in the reaction and workup, as well as organic phases which contain byproducts and aqueous phases which contain inorganic acids and salts. An ecologically appropriate workup and disposal of all this waste is very complicated and costly. This method is unsuitable for the industrial scale for these reasons too.

Although the methods of WO 98/39298 provide products with purities of up to 98 to 99%, the maximum yield of DCFNA is only 76%. In addition, large reaction volumes are required (for example a 12 liter vessel for a 500 g feed) because otherwise there is occurrence of intermediate states which are difficult to stir.

All the prior art methods for producing DCFNA provide very fine products having average particle sizes in the range from 30 to 75 $\mu$m. They are therefore difficult to filter, require long filtration times and, after the filtration, still contain relatively large amounts of mother liquor including the impurities present in the mother liquor.

There is thus still a need for a method for producing DCFNA which can be carried out easily and reliably on the industrial scale, provides the product in good yield, good space yield and good purity, which is economically advantageous and can be carried out with low expenditure on apparatus.

A method for the production of 2,6-dichloro-5-fluoronicotinic acid (DCFNA) by hydrolyzing 2,6-dichloro-5-fluoro-3-cyanopyridine (DCFN nitrile) has now been found and is characterized in that a) DFCN nitrile is dissolved at 70 to 90° C. in sulfuric acid with a concentration of 90 to 99% by weight and hydrolyzed at 70 to 100° C. to the corresponding carboxamide, b) then the reaction mixture is cooled to a temperature in the range from 10 to 65° C., c) subsequently water is metered in until the concentration of sulfuric acid is 55 to 75% by weight (calculated on the basis of the sulfuric acid employed in stage a) and the water employed in stage c)), keeping the temperature between 30 and 65° C. during the addition of the first quarter of the water and keeping the temperature between 50 us 80° C. during the addition of the second quarter of the water, and d) the hydrolysis to DCFNA is completed at 70 to 110° C.

DFCN nitrile can be employed in stage a) as such or else in dissolved form. If it is wished to employ it in dissolved form, care must be taken that the solvent does not react with conc. sulfuric acid. Examples of suitable solvents are chlorinated aliphatic compounds. Those preferred have boiling points below 80° C., and preferably have boiling points below 70° C., because they then distill out of the reaction mixture.

It is also possible to employ the DCFN nitrile dissolved or suspended in phosphorus oxychloride as it results, for example, from its production. It is advantageous to remove some of the phosphorus oxychloride derived from the production of DCFN nitrile, for example by distillation, before mixing with the sulfuric acid.

The dissolving and the hydrolysis in stage a) is preferably carried out at temperatures in the range from 75 to 85° C.

If insufficient water for hydrolyzing DCFN nitrile to the corresponding carboxamide has been introduced with the sulfuric acid, further water is added during stage a). The total amount of water (contained in the sulfuric acid plus water added as such where appropriate) for stage a) is preferably 1 to 1.5 mol per mol of DCFN nitrile employed.

The amount of sulfuric acid to be employed in stage a) can be, for example, 1 to 6 times the amount by weight based on DCFN nitrile. The time for the addition of the sulfuric acid and of the DCFN nitrile may vary within wide limits and be, for example, between 0.5 and 10 hours.

The cooling to be carried out in stage b) preferably takes place to temperatures in the range from 20 to 60° C.

It is an essential feature of the present invention that stages c) and d) be carried out entirely with increasing temperature. It is advantageous in this connection to combine within the ranges stated in each case high concentrations of sulfuric acid with low temperatures and low concentrations of sulfuric acid with high temperatures, or to select both the concentration of sulfuric acid and the temperature approximately from the middle of the ranges indicated in each case.

The water to be added in stage c) can be metered in various ways, for example a constant quantity per unit time can be added throughout the addition time. This mode of addition is easy to control. It is also possible for the water to be metered in initially in a smaller quantity per unit time and to change to a larger quantity per unit time during the addition. It is possible in this way where appropriate to shorten the total metering time required, but special care must be taken that the temperature limits to be complied with are not exceeded.

The metering time for the water depends essentially on how quickly the heat which is liberated can be removed while maintaining the required maximum temperatures, and can be, for example, in the range from 1 to 10 hours.

The temperature can be controlled during the addition of the water in a quasi-adiabatical or quasi-isothermal manner or in another manner. A quasi-adiabatic procedure can be such that, before the addition of the water, the reaction mixture is brought to a temperature of, for example, 30 to 40° C., where appropriate also to an even lower temperature, for example 10 to 30° C., and the heat which is produced is removed so that the reaction mixture heats initially to, for example, 30 to 65° C. and later to, for example, 50 to 80° C.

An example of a quasi-isothermal procedure is to meter in the total quantity of water at, for example, 50 to 65° C.

The quasi-adiabatic and the quasi-isothermal procedure can also be combined, for example, working quasi-adiabatically at the start of the addition of water, for example during addition of the first 10 to 30% by weight of the water, and adding the remaining water in a quasi-isothermal procedure at, for example, 50 to 80° C.

Other ways of metering the water to be added are also conceivable.

The hydrolysis to DCFNA is completed at temperatures in the range from 70 to 110° C. (=stage d)). At a given acid concentration, the time required for this hydrolysis depends essentially on the temperature. If the sulfuric acid concentration is, for example, 63 to 68% by weight (calculated from the added sulfuric acid and the added water), then 1.5 to 3 hours for example are required at temperatures above 95° C., 3 to 8 hours for example at temperatures between 80 and 95° C., and up to 48 hours for example at temperatures below 80° C., to complete the hydrolysis.

The reaction mixture present after stage d), which frequently already contains precipitated DCFNA, can be worked up for example by initially cooling it, for example, to 10 to 30° C., then filtering off the DCFNA present, washing it, for example with water, and drying it.

The method of the invention has a number of surprising advantages. Thus, the yield of DCFNA in it is usually more than 85% of theory, frequently 90% of theory and above. The method is easy to carry out, the carboxamide intermediate need not be isolated, and no organic solvents are required. The product results in high purity, contains less than 1% by weight of decomposition products, frequently even less than 0.5% by weight of decomposition products, and can be used further without further purification. The method is particularly environmentally compatible because no nitrous gases, nor salt-containing wastewater nor polluted organic phases are produced, nor is the manipulation of solvents and other aids particularly complicated. In addition, the method can be carried out in conventional apparatus on the industrial scale without difficulty. The reaction volumes required for the method of the invention are small.

Another advantage of the method of the invention is that the resulting DCFNA is less fine than in prior art methods. For this reason, DCFNA produced according to the invention can be filtered more easily and in a shorter time and, after the filtration, it contains only small amounts of mother liquor.

The DCFNA produced according to the invention has average particle sizes above 80 $\mu$m, for example in the range from 90 to 180 $\mu$m.

It is exceptionally surprising that this large number of advantages can be achieved with the method of the invention because, as is evident from the stated prior art, several attempts have already been made to produce DCFNA in a satisfactory manner on the industrial scale. Only the method of the invention has now provided a simple and efficient method for producing DCFNA.

The present invention also relates to 2,6-dichloro-5-fluoronicotinic acid containing less than 1% by weight of decomposition products, and 2,6-dichloro-5-fluoronicotinic acid which has an average particle size above 80 $\mu$m.

EXAMPLES

Example 1

4420 kg of 96% by weight sulfuric acid were added over the course of 6 hours at 45 to 50° C. to a solution of 1185 kg of 2,6-dichloro-5-fluoronicotinonitrile in 5300 kg of methylene chloride, and the mixture was then heated to 80° C., whereupon the methylene chloride distilled out. The resulting solution was cooled to 25° C. While stirring efficiently, initially 400 kg of water were metered in so that the temperature reached, but did not exceed, 75° C. (quasi-adiabatic procedure). A further 2000 kg of water were then pumped in over the course of 4 hours, and the temperature was kept at 75° C. by slight cooling. The mixture was then heated to 90° C. and stirred at this temperature for 8 hours. The resulting suspension was then cooled to 20° C., and the solid which was present was filtered off and washed twice with 1100 l of water each time. The moist product was dried in a paddle drier at 60° C. and 200 mbar to result in 1173 kg of dry 2,4-dichloro-5-fluoronicotinic acid (90.0% of theory). It contained less than 0.5% by weight of decomposition products and had an average particle size of 100 μm.

Example 2

305 kg of 96% by weight sulfuric acid were heated to 78° C. and, over the course of 5 hours, a solution of 95 kg of 2,6-dichloro-5-fluoronicotinonitrile in 500 kg of methylene chloride was added dropwise. The methylene chloride distilled out during this time. After cooling to 50° C., 165 kg of water were pumped in at a temperature of 50° C. over the course of 4 hours. The mixture was then stirred at 90° C. for 7 hours, during which the product gradually precipitated. Workup of the reaction mixture in analogy to example 1 resulted in 91.4 kg of 2,6-dichloro-5-fluoronicotinic acid (corresponding to 87.0% of theory). The latter contained less than 0.5% by weight of decomposition products and had an average particle size of 100 μm.

Example 3

The procedure was as in example 1 but the 2,6-dichloro-5-fluoronicotinonitrile was employed not as solution in methylene chloride but as solid. The results were the same as in example 1.

Example 4

A solution of 2,6-dichloro-5-fluoronicotinonitrile obtained by chlorination of 0.5 mol of 2,6-dihydroxy-5-fluoronicotinonitrile in 2.75 mol of POCl₃ was initially concentrated by distilling out 240 g of POCl₃. After cooling to 45° C., 395 g of 96% by weight sulfuric acid were added dropwise over the course of 1 hour, during which the temperature of the receiver was kept at 38 to 42° C. by cooling. It was then stirred at an internal temperature of 80° C. for 2 hours, and a fine suspension was obtained. At an internal temperature of 60° C., 190 g of water were pumped in over the course of 3 hours, and then the mixture was stirred at 90° C. for 8 hours. Cooling to 5° C. was followed by filtration through an acid-resistant filter and washing 3 times with 100 ml of water each time. This resulted in 85 g of moist product, from which 79 g of 2,6-dichloro-5-fluoronicotinic acid were obtained by drying. The yield of all the stages was 75% of theory, the content of decomposition products was 0.9% by weight and the average particle size was 150 μm.

Comparative Example 1

This shows that the yield stated in the Chem. Pharm. Bull. reference is not in fact achieved.

60 ml of 96% by weight sulfuric acid were introduced into a 250 ml flask and, at 40 to 45° C., 30 g of 2,6-dichloro-5-fluoronicotinonitrile were added. The mixture was stirred until the solution was complete and was then heated at 70 to 75° C. for 1 hour. Then, over the course of 30 minutes, 60 ml of water were added dropwise, during which the internal temperature was kept at 90 to 95° C. by cooling. The mixture was subsequently stirred at 105° C. for 1.5 hours and finally, at 90° C., a further 60 ml of water were added and the mixture was stirred at room temperature for 2 hours. The product produced in this way was removed by filtration through a glass suction filter funnel, washed twice with 30 ml of water each time and dried in a vacuum oven at 50° C. and 200 mbar. 27.7 g of 2,6-dichloro-5-fluoronicotinic acid (84.1% of theory), which additionally contained 6% by weight of a decomposition product and therefore could not be used further in this form, were obtained. The product produced in this way had an average particle size of 75 μm.

Comparative Example 2

This shows that usable results are not obtained in accordance with the Chem. Pharm. Bull. reference even if the time for dilution between the two hydrolysis stages is lengthened. The product was isolated from a 64% by weight sulfuric acid because it was possible in this case to keep some of the decomposition products in solution.

The procedure was initially as in comparative example 1, but the first 60 ml of water for dilution were added over the course of 6 hours at 90 to 95° C. The mixture was then stirred at 105° C. for 1.5 hours and finally cooled to room temperature. 28.5 g of crude 2,6-dichloro-5-fluoronicotinic acid which contained 14.7% by weight of decomposition products (based on the main product) were obtained.

Comparative Example 3 a) Procedure disclosed in WO 98/39298 but without the complicated purification described.

140 ml of 96% by weight sulfuric acid were introduced into a 1 l stirred flask with reflux condenser, stirrer, internal thermometer and dropping funnels, and 30 g of 2,6-dichloro-5-fluoronicotinonitrile were added. The mixture was stirred at 70° C. for 2 hours and then cooled to 5° C. Then a solution of 24 g of sodium nitrite and 30 ml of water was slowly added dropwise, and the temperature was kept at 35° C. The mixture was subsequently stirred at 5° C. for 15 minutes and then at 50° C. for 3 hours. After cooling to 25° C., the suspension was filtered through a sintered glass suction funnel and washed twice with water. Initially 65 g of moist product were obtained, and from this were obtained by drying at 50° C. 31.3 g of crude 2,6-dichloro-5-fluoronicotinic acid as a fine powder. This had a content of 95.4% by weight and an average particle size of 35 μm. The yield was 90.5% of theory.

b) Procedure disclosed in WO 98/39298

22 g of the 2,6-dichloro-5-fluoronicotinic acid prepared in a) were dissolved in 100 g of water which contained 11 g of sodium carbonate at 30° C. At room temperature, while stirring efficiently, 10% by weight aqueous hydrochloric acid was added dropwise until the pH reached 1. The precipitated 2,6-dichloro-5-fluoronicotinic acid was filtered off with suction and washed with water. Initially 31 g of moist product were obtained and from this were obtained, by drying, 20.5 g of purified product which had a content of 99.5% by weight and an average particle size of 50 μm. The yield from the reprecipitation was 97.2% of theory.

Comparative Example 4

As disclosed in EP-A 160 578.

a) 30 g of 2,6-dichloro-5-fluoronicotinonitrile were heated in a mixture of 150 g of acetic acid, 14.5 g of water and 14.5 g of 100% by weight sulfuric acid under reflux (116 to 117° C.) for 16 hours. The resulting solution was analyzed by HPLC. It contained (standardized to 100%) 50.1% of 2,6-dichloro-5-fluoronicotinic acid, 4.9% by weight of 2,6-dichloro-5-fluoronicotinamide, 39.3% of unreacted starting material and 4.7% of decomposition products.

b) In a repetition of this example the mixture was heated to reflux for 32 hours instead of 16 hours. The solution then analyzed by HPLC contained 65.1% of 2,6-dichloro-5-fluoronicotinic acid, 3.2% of 2,6-dichloro-5-fluoronicotinamide, 23.4% of unreacted starting material and 8.2% of decomposition products.

What is claimed is:

1. A method for the production of 2,6-dichloro-5-fluoronicotinic acid by hydrolyzing 2,6-dichloro-5-fluoro-3-cyanopyridine comprising
   (a) dissolving 2,6-dichloro-5-fluoro-3-cyanopyridine at 70 to 90° C. in sulfuric acid having a concentration of 90 to 99% by weight and hydrolyzing the 2,6-dichloro-5-fluoro-3-cyanopyridine at 70 to 100° C. to the corresponding carboxamide,
   (b) cooling the resultant reaction mixture to a temperature in the range from 10 to 65° C.,
   (c) metering in water until the concentration of sulfuric acid is 55 to 75% by weight (calculated relative to the sulfuric acid employed in stage (a) and the water employed in stage (c)) while keeping the temperature between 30 and 65° C. during the addition of the first quarter of the water and keeping the temperature between 50 and 80° C. during the addition of the second quarter of the water, and
   (d) completing hydrolysis of the resultant mixture to 2,6-dichloro-5-fluoronicotinic acid at 70 to 110° C.

2. A method according to claim 1 wherein the 2,6-dichloro-5-fluoro-3-cyanopyridine is used as such, in dissolved form, or dissolved or suspended in phosphorus oxychloride.

3. A method according to claim 1 wherein stage (a) is carried out at temperatures in the range from 75 to 85° C.

4. A method according to claim 1 wherein the total amount of water in stage (a) is 1 to 1.5 mol per mol of 2,6-dichloro-5-fluoro-3-cyanopyridine and the amount of sulfuric acid is 1 to 6 times the amount by weight of 2,6-dichloro-5-fluoro-3-cyanopyridine.

5. A method according to claim 1 wherein stage (b) is carried out at temperatures in the range from 20 to 60° C.

6. A method according to claim 1 wherein the metering time for the water in stage (c) is in the range from 1 to 10 hours.

7. A method according to claim 1 wherein stage (c) is carried out by a quasi-adiabatic procedure, a quasi-isothermal procedure, or a mixed quasi-adiabatic and quasi-isothermal procedure.

8. A method according to claim 1 wherein the reaction mixture after stage (d) is worked up by cooling, and filtering, washing, and drying the resultant solid 2,6-dichloro-5-fluoronicotinic acid.

9. 2,6-Dichloro-5-fluoronicotinic acid containing less than 1% by weight of decomposition products formed during preparation thereof.

10. 2,6-Dichloro-5-fluoronicotinic acid having a particle size above 80 $\mu$m.

* * * * *